United States Patent [19]

Wright

[11] 3,939,216

[45] Feb. 17, 1976

[54] PROCESS FOR THE PREPARATION OF NEOPENTYL GLYCOL

[75] Inventor: Roger L. Wright, Longview, Tex.

[73] Assignee: Eastman Kodak Company, Rochester, N.Y.

[22] Filed: June 26, 1974

[21] Appl. No.: 483,321

[52] U.S. Cl............ 260/635 P; 260/602; 260/637 P
[51] Int. Cl.².......................................... C07C 29/00
[58] Field of Search...................... 260/635 P, 637 P

[56] References Cited
UNITED STATES PATENTS

| | | | |
|---|---|---|---|
| 2,223,421 | 12/1940 | Hubacher et al. ............... | 260/637 P |
| 2,400,724 | 5/1946 | Walker............................ | 260/635 P |
| 2,780,655 | 2/1957 | Yalowitz.......................... | 260/637 P |
| 2,811,562 | 10/1957 | Hagemeyer..................... | 260/635 P |
| 2,895,996 | 7/1959 | Wright et al. .................. | 260/635 P |
| 3,340,312 | 9/1967 | Duke et al....................... | 260/635 P |
| 3,776,963 | 12/1973 | Zey et al. ....................... | 260/637 P |

*Primary Examiner*—Joseph E. Evans
*Attorney, Agent, or Firm*—Edward R. Weber; Daniel B. Reece, III

[57] ABSTRACT

A process for recovery of neopentyl glycol from a waste stream comprising neopentyl glycol and water, wherein said waste stream is contacted with isobutyraldehyde and subsequently separated into an organic stream comprising neopentyl glycol and isobutyraldehyde and an aqueous stream essentially free of neopentyl glycol.

4 Claims, 1 Drawing Figure

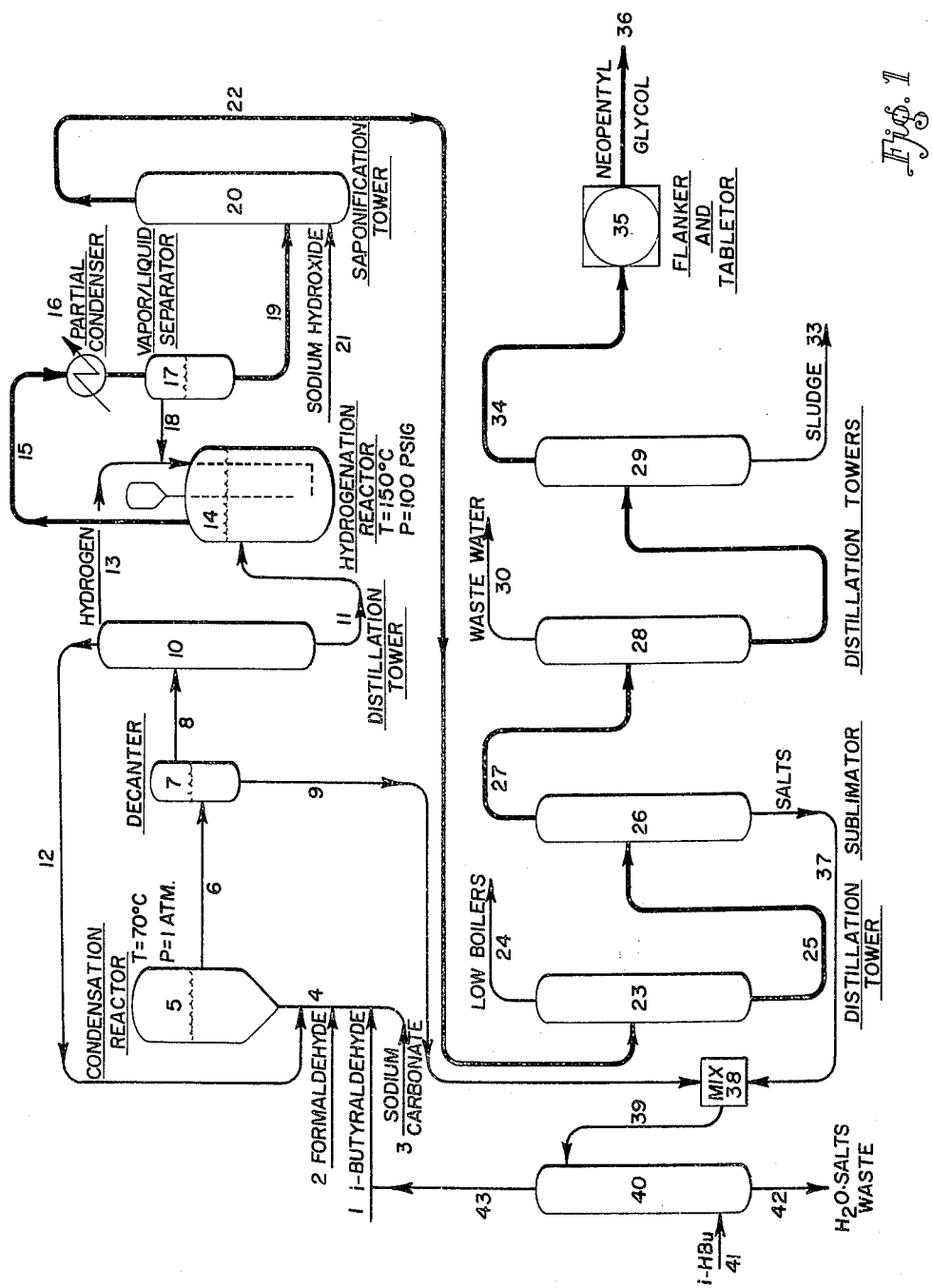

PROCESS FOR THE PREPARATION OF NEOPENTYL GLYCOL

This invention relates to an improved process for recovering neopentyl glycol. More specifically, this invention relates to an improved process for recovering small quantities of neopentyl glycol from waste streams produced in the manufacturing process.

Neopentyl glycol (2,2-dimethylpropane-1,3-diol) is a white, crystalline solid with a melting point of 130°–131°C. It is produced by the condensation of isobutyraldehyde with formaldehyde is an aldol type reaction, and the subsequent reduction of the intermediate condensation product to neopentyl glycol. Hydroxypivaldehyde which is formed as the intermediate condensation product in the process, is a highly reactive compound. It has a tendency to form an ester by a Tischenko reaction. When catalyzed hydrogenation is employed to reduce the hydroxypivaldehyde to the desired diol, the crude neopentyl glycol is contaminated with as much as 10–15 percent of the neopentyl glycol ester of hydroxypivalic acid. This ester is not stable when the crude reaction mixture is distilled. For maximum recovery of neopentyl glycol the crude reaction product is saponified with caustic. Distillation of the saponified mixture in the presence of sodium salts of hydroxypivalic acid and other organic acids present in the impure reaction mixture results in considerable decomposition of the neopentyl glycol and a very impure product. Various means have been suggested for purification of the crude neopentyl glycol, for example, extraction with a solvent medium containing a low boiling point ketone such as acetone, direct separation of the neopentyl glycol from the crude reaction product by vacuum distillation, fractional crystallization, etc., have all been proposed. Each of these proposed methods, however, suffered from one or more infirmities which made them commercially undesirable.

Hagemeyer and Wright U.S. Pat. No. 2,895,996, disclose a process wherein a substantially pure solution of neopentyl glycol in water is obtained by steam sublimation of the crude reaction product at reduced pressures. A subsequent distillation of the neopentyl glycol/water mixture removes the water and yields substantially pure neopentyl glycol. An important variable in operation of the steam sublimator is the sublimator base temperature. At temperatures below about 70°C., the percent neopentyl glycol in the overhead from the sublimator is so low that the process is uneconomical, whereas at temperatures above 140°C., appreciable decomposition of the neopentyl glycol occurs. The base temperature of the sublimator can be controlled to a limited extent by controlling the vacuum in the sublimator, however, when the maximum sublimator vacuum is reached, the sublimator base temperature will gradually increase as sodium salts accumulate in the sublimator base. When the base temperature reaches 140°C., the operation must be stopped and the sublimator base sludged and washed out. This periodic shut-down and wash-out is necessary for an economical operation. Continuous purge of the sublimator base to maintain the base temperature below 140°C. has heretofore resulted in so much lost neopentyl glycol that the process has been considered uneconomical.

It is, therefore, an object of my invention to provide a process wherein the sublimator purification can be operated continuously without an unacceptable loss of product neopentyl glycol.

Another object of my invention is to provide a process wherein the organic components of certain waste streams are recovered and reused, rather than discharged to pollution control facilities.

Yet another object of my invention is to provide an improvement in the process which permits more complete recovery of product neopentyl glycol.

These and other objects and advantages of this invention will become apparent from the following description and appended claims.

The process of my invention consists of an improvement to the aforementioned neopentyl glycol manufacturing process (Hagemeyer and Wright) whereby two waste streams are combined to form a fluid mass capable of being extracted, extracting this mixture with isobutyraldehyde, and utilizing the isobutyraldehyde extract as feed for the aldol reactor. This process innovation results in the recovery of sufficient neopentyl glycol to increase the effective process yields by 3 percent to 5 percent. In addition, it yields an aqueous waste stream which is substantially free of organic matter. This waste stream requires much less treatment than was required for the waste streams resulting from the process as previously practiced.

The two major effluent streams upon which my invention depends contain unreacted product and large amounts of sodium salts. These streams are the aqueous catalyst-containing stream from the reactor decanter, and the base from the sublimator. Not only does the process of my invention result in recovery of materials previously lost in the waste streams, it further allows continuous sublimator operation. This eliminates the need for periodic shut-down, and allows the efficiency of steadystate operation. By eliminating the periodic shut-down, the productive capacity of the facility may be increased by from about 10 percent to about 15 percent.

The following description of the process according to my invention has reference to FIG. 1, which is a schematic flow diagram of one embodiment of the overall process. Isobutyraldehyde is continuously fed via line 1, and formaldehyde, e.g., an aqueous solution of formaldehyde, is continuously fed via line 2. An aqueous sodium carbonate catalyst solution is continuously fed via line 3. The feed streams are combined in line 4, and fed into the aldol condensation reactor 5. A portion of the reacted mixture is withdrawn from reactor 5 via line 6, and introduced into decanter 7, wherein the aqueous and organic phases are separated. The aqueous phase is withdrawn via line 9. The organic phase containing hydroxypivaldehyde, isobutyraldehyde, and other byproducts, is withdrawn via line 8 and introduced into distillation tower 10. Volatile materials are taken off overhead and recycled to the condensation reactor via line 12. Base take-off from the distillation tower is introduced into hydrogenation reactor 14 via line 11. Hydrogen is introduced via line 13. The reduced mixture is withdrawn via line 15, passed through partial condenser 16, and into vapor-liquid separator 17. The vapor phase is reintroduced into the hydrogenation reactor via line 18, whereas the liquid phase is withdrawn via line 19 and introduced into saponification tower 20. Sodium hydroxide is introduced into the saponification tower via line 21 and the saponified mixture is withdrawn via line 22 and introduced into distillation tower 23. Low boiling components are withdrawn overhead via line 24 and the product mixture is withdrawn via line 25 and introduced into steam sublimator 26. An essentially pure neopentyl glycol-water mixture is withdrawn overhead from sublimator 26 via line 27, and introduced into purification distillation towers 28 an 29, wherein water is removed overhead via line 30 and high-boiling impurities are removed via line 33. Substantially pure neopentyl glycol is withdrawn via line 34 and introduced into flaker 35 to yield commercial neopentyl glycol 36.

In the improvement according to my invention, the aqueous, catalyst-containing stream, line 9, and the sublimator base-stream, line 37, are mixed 38 and introduced via line 39 into an extracter 40. Isobutyraldehyde 41 introduced into extracter 40, extracts essentially all of the organic material introduced in aqueous stream 39. The isobutyraldehyde/organic extract removed from the extracter via line 43 is introduced into line 1 and utilized as feed for the condensation reactor. The substantially organic free water-containing stream from the base of the extracter is removed via line 42.

In a preferred continuous embodiment of my invention, a constant fraction of the base in the stream sublimator is drawn off so as to maintain the base sublimator temperature at from about 130°C. to about 140°C. when the sublimator is under a vacuum of 20 inches of water. In normal operation, this base take-off will amount to from about 5 percent to about 10 percent of the total sublimator feed. Typical analysis of this base stream is 50 percent to 60 percent neopentyl glycol, 40 percent to 30 percent sodium salts, and 10 percent water. This sublimator base stream is then mixed with the spent catalyst stream from the reactor decanter, which is typically about five times as great in volume. Typical analysis of the aqueous stream from the decanter is 87 percent water, 8 percent to 12 percent sodium salts, 1.5 percent to 2.0 percent isobutyraldehyde, 0.75 percent to 1.25 percent neopentyl glycol, and 0.3 percent to 0.8 percent hydroxypivaldehyde. When mixed, the two streams will produce a mixture with a typical analysis of 72 percent water, 16 percent sodium salts, 1.5 percent isobutyraldehyde, 10 percent neopentyl glycol, 0.5 percent hydroxypivaldehyde. The composition of this stream is not critical. Normally it is desirable that enough water be present so that all ingredients are liquid at ambient temperatures, although this is not essential as any temperature may be utilized so long as it is above the freezing point and below the boiling point of all components of the mixture. This mixed stream is then extracted in a continuous extracter with isobutyraldehyde, and the extract is fed to the condensation reactor. The extraction efficiency is greater than 99.9 percent with regard to recovery of neopentyl glycol and hydroxypivaldehyde. The water-containing stream leaving the extractor contains less than about 0.05 percent hydroxypivaldehyde, less than about 0.05 percent neopentyl glycol, about 1.3 percent isobutyraldehyde, about 18 percent sodium salts, about 80.7 percent water. Because of the extremely low organic content of this stream, subsequent pollution-control processing is greatly facilitated.

Inasmuch as the isobutyraldehyde used as the extractant is one of the feed materials, no separate solvent recovery is required. The isobutyraldehyde extract is fed directly to the aldol reactor. The presence of neopentyl glycol and hydroxypivaldehyde in this stream has been found to have no adverse effect on the reaction rate.

It was quite surprising that isobutyraldehyde could be used to extract organic materials with such high efficiency, and that the recycle of the extracted materials into the aldol reactor would have no adverse effects on the reaction. Neopentyl glycol has a solubility of 90 percent in water. It was therefore quite unexpected that it could be removed from a water stream by isobutyraldehyde with an efficiency of greater than 99.9 percent. The extraction coefficient for neopentyl glycol in water and isobutyraldehyde was determined to be approximately 5.5. The extraction coefficient is defined as the pounds of neopentyl glycol in isobutyraldehyde per pound of neopentyl glycol in water. This would result in a minimum isobutyraldehyde to water feed ratio for this system of about 0.18 to 1.0. The maximum ratio is limited only by the capacity of the aldol reactor as it would be inconvenient to use more isobutyraldehyde than could be fed to the reactor. Normal isobutyraldehyde feed to the process is about 1.5 times the water flow, which is approximately 8 times the minimum required.

The unexpected discovery that recycled neopentyl glycol in the isobutyraldehyde stream would have no effect on the aldol condensation reaction is confirmed by a comparison of otherwise identical runs in an aldol reactor. In one run, 10 percent neopentyl glycol, based on the isobutyraldehyde content, is added. Both runs are made at atmospheric pressure and 65°C. The reaction rate constant is 0.56 liters per gram mole per hour with neopentyl glycol present, and 0.59 liters per gram mole per hour without neopentyl glycol. This difference in reaction rate is considered to be insignificant and within ordinary experimental error. No increase in impurities due to the presence of neopentyl glycol is observed. The neopentyl glycol appears to be inert in the aldol reactor, the only effect being a lowering of effective reactor volume similar to that experienced if an inert diluent is used.

The surprising efficiency of isobutyraldehyde as an extractant for the organic materials is further illustrated by reference to the following example.

EXAMPLE 1

Using a countercurrent flow bench-scale extactor consisting of a 1½ inch diameter by 10 foot long glass column filled with Penn State packing, a stream representing the mixed sublimator-decanter effluent waste streams is fed 8 inches below the top of the extracter. This stream has the following analysis: 71.5 g. neopentyl glycol, 6.5 g. hydroxypivaldehyde, 1.3 g. trimethylpentanediol, 3.9 g. isobutyraldehyde, 3.9 g. methanol, 52.0 g. sodium carbonate, 19.5 g. sodium butyrate, and 491.4 g. water. An isobutyraldehyde stream having the following analysis; 568.4 g. isobutyraldehyde, and 11.6 g. water, is introduced 8 inches above the base of the extractor. From the top of the extracter is withdrawn a stream having the following analysis: 71.5 g. neopentyl glycol, 6.5 g. hydroxypivaldehyde, 1.3 g. trimethylpentanediol, 567.6 g. isobutyraldehyde, 3.3 g. methanol, 10 ppm. sodium butyrate, and 19.8 g. water. This stream is suitable for feed to the aldol condensation reactor. From the base of the extracter is drawn a water stream having the following analysis: less than 0.3 g. neopentyl glycol, less than 0.3 g. hydroxypivaldehyde, less than 0.3 g. trimethylpentanediol, 4.7 g. isobutyraldehyde, 0.6 g. methanol, 52.0 g. sodium carbonate, 19.5 g. sodium butyrate, and 483.2 g. water. Examination of these streams serves to illustrate the surprising efficiency of the isobutyraldehyde as an extractant for the organic materials contained in the mixed sodium salt-containing effluent stream.

EXAMPLE 2

This example demonstrates the fact that neopentyl glycol introduced into the aldol reaction has minimal effect on the reaction. A typical aldol reactor is set up using a 2-liter, three-necked flask fitted with a stirrer, thermowell, condenser and steam heater. using such a set-up, two runs are made at 65°C. plus or minus 3°C. utilizing sodium carbonate as a catalyst. Feed compositions for the two runs are shown in Table I. The product is sampled at specific time intervals and analyzed for hydroxypivaldehyde, neopentyl glycol and neopentyl glycol monoisobutyrate, low-boilers and high-boilers. The results of these analyses are shown in Table II. It will be noted that the hydroxypivaldehyde content is approximately the same; the neopentyl glycol content in Run 1 is different by the approximate amount of neopentyl glycol added to the feed; the low-boilers are only very slightly increased; and the high-biolers are of the same order of magnitude. These comparative runs demonstrate that neopentyl glycol passes through the aldol reaction essentially unchanged and without effecting the reaction.

TABLE I

| | Feed Composition | |
| --- | --- | --- |
| | Run 1 | Run 2 |
| Isobutyraldehyde | 7.5 moles | 7.5 moles |
| Formaldehyde | 1.5 moles | 1.5 moles |
| Neopentyl Glycol | .49 moles* | — |
| Sodium Carbonate (Catalyst) | 3.23% of total feed | 3.23% of total feed |

*9.2% based on total weight of organic feed

TABLE II

| | Product Composition (Weight Percent) | | | | | |
| --- | --- | --- | --- | --- | --- | --- |
| | Run 1 | | | Run 2 | | |
| Time (mins.) | 15 | 60 | 120 | 15 | 60 | 120 |
| Hydroxypivaldehyde | 14.31 | 20 | 20.5 | 14.04 | 19.81 | 19.29 |
| Neopentyl glycol & neopentyl glycol monoisobutyrate | 10.1 | 11.4 | 13.3 | 2.2 | 3.44 | 3.15 |
| Low Boilers | .55 | .55 | .55 | Trace | Trace | Trace |
| High Boilers | .17 | .93 | 1.48 | .13 | .58 | 1.33 |

Although the invention has been described in considerable detail with particular reference to certain preferred embodiments thereof, variations and modifications can be effected within the spirit and scope of the invention as described hereinabove and as defined in the appended claims.

I claim:

1. In a process for producing neopentyl glycol of high purity wherein isobutyraldehyde and formaldehyde are reacted in a condensation reactor in the presence of a condensation catalyst to form a reaction mixture containing hydroxypivaldehyde; said reaction mixture is separated into an organic component containing hydroxypivaldehyde and an aqueous component containing the spent catalyst; which hydroxypivaldehyde-containing component is then reduced to produce neopentyl glycol; saponified with caustic to cleave hydroxypivaldehyde esters present in the crude neopentyl glycol-containing reaction mixture; and the resulting mixture sublimated by passing steam through the saponified reaction mixture in a sublimator, the sublimator being at a temperature of about 70°C. to about 140°C.; the improvement which comprises mixing residue from the sublimator base with the aqueous spent catalyst-containing component from the condensation reactor to provide a liquid mixture, extracting the organic materials from the mixture with sufficient isobutyraldehyde to provide a minimum isobutyraldehyde to water ratio in the extractor of about 0.18 to 1.0, and utilizing the resultant isobutyraldehyde extract as a feed to the condensation reactor.

2. In a continuous process for producing neopentyl glycol of high purity wherein isobutyraldehyde is reacted with formaldehyde in a condensation reactor to form an aqueous stream containing spent catalyst and an organic stream containing hydroxypivaldehyde, which organic stream is then reduced to produce neopentyl glycol, saponified with caustic to cleave hydroxypivaldehyde esters present in the crude neopentyl glycol-containing reaction mixture, and the resulting saponified reaction mixture sublimated by passing steam through said saponified reaction mixture in a sublimator, the said sublimator being at a temperature of from about 70°C. to about 140°C.; the improvement which comprises continuously withdrawing a base stream from the sublimator, which stream comprises neopentyl glycol, sodium salts and water, in a quantity sufficient to permit continuous operation of the sublimator combining said base steam with the aqueous spent catalyst-containing stream from the condensation reactor to provide a liquid mixed stream, extracting the neopentyl glycol from said mixed streams with sufficient isobutyraldehyde to provide a minimum isobutyraldehyde to water ratio of 0.18 to 1.0, and utilizing the neopentyl gylcol/isobutyraldehyde extract as a feed to the said condensation reactor.

3. A process according to claim 2 wherein the base temperature of the sublimator is held below about 140°C.

4. A process according to claim 3 wherein the base temperature of the sublimator is held at about 130°C. to about 140°C.

* * * * *

UNITED STATES PATENT OFFICE
CERTIFICATE OF CORRECTION

Patent No. 3,939,216      Dated February 17, 1976

Inventor(s) Roger L. Wright

It is certified that error appears in the above-identified patent and that said Letters Patent are hereby corrected as shown below:

Column 6, line 36, at the beginning of the line, insert a semicolon (;) after "mator".

Column 6, line 36, delete "steam" and insert therefor ---stream---.

Signed and Sealed this fourth Day of May 1976

[SEAL]

Attest:

RUTH C. MASON  
Attesting Officer

C. MARSHALL DANN  
Commissioner of Patents and Trademarks